United States Patent [19]

Stroech et al.

[11] Patent Number: 5,218,002

[45] Date of Patent: Jun. 8, 1993

[54] INSECT- AND MITE-REPELLING METHOD

[75] Inventors: Klaus Stroech, Solingen; Bernd-Wieland Krüger, Bergisch Gladbach; Peter Hoever; Günther Nentwig, both of Cologne, all of Fed. Rep. of Germany

[73] Assignee: Bayer Aktiengesellschaft, Leverkusen, Fed. Rep. of Germany

[21] Appl. No.: 706,129

[22] Filed: May 28, 1991

[30] Foreign Application Priority Data

Jun. 6, 1990 [DE]  Fed. Rep. of Germany ....... 4018070

[51] Int. Cl.$^5$ .............................. A01N 43/84
[52] U.S. Cl. ................. 514/919; 514/237.5; 424/403; 544/169
[58] Field of Search ............ 544/169; 514/237.5, 514/919; 424/403

[56] References Cited

U.S. PATENT DOCUMENTS 3,296,306  1/1967  Doering et al. ................. 544/169
4,389,401  6/1983  Smolanoff ....................... 514/919

FOREIGN PATENT DOCUMENTS 2050522  3/1971  France .

OTHER PUBLICATIONS

Chemical Control of Insect Behavior, Theory and Application 1902.
Pest Control, Strategies for the Future, Nat. Academy of Sciences, Washington, D.C. 197, "Attractants and Repellants for Insect Pest Control", Morton Beroza 1962.
Chemie der Pflanzenschutz- und Schädlings-bekämpfungsmittel, vol. 1, p. 487 1970.
Chemistry of Pesticides, John Wiley & Sons (1983).

*Primary Examiner*—Robert W. Ramsuer
*Attorney, Agent, or Firm*—Sprung Horn Kramer & Woods

[57] ABSTRACT

Insect- and mite-repelling new morpholinoureas of the formula (I)

$$\begin{array}{c} R^1\;R^2\quad R^3\;R^4 \\ \diagdown\diagup\quad\diagdown\diagup \\ \qquad\qquad\qquad\qquad O\qquad R^9 \\ \qquad\qquad\qquad\qquad\|\qquad\diagup \\ O\qquad\qquad N-C-N \\ \qquad\qquad\qquad\qquad\qquad\diagdown \\ \qquad\qquad\qquad\qquad\qquad\;\;R^{10} \\ \diagup\diagdown\quad\diagup\diagdown \\ R^8\;R^7\quad R^6\;R^5 \end{array} \qquad (I)$$

in which the radicals $R^1$ to $R^8$ can be identical or different and represent hydrogen, optionally substituted alkyl, optionally substituted alkenyl, optionally substituted alkynyl, optionally substituted cycloalkyl or optionally substituted phenyl, or where the radicals $R^1$ and $R^4$ and/or $R^5$ and $R^8$ in each case together form a carbocyclic ring, $R^9$ represents optionally substituted alkyl, optionally substituted alkenyl, optionally substituted alkynyl, optionally substituted cycloalkyl or optionally substituted benzyl, and $R^{10}$ represents hydrogen, optionally substituted alkyl, optionally substituted alkenyl, optionally substituted benzyl or optionally substituted cycloalkyl, or where $R^9$ and $R^{10}$ together represent an optionally substituted polyalkylene radical which is optionally interrupted by hetero atoms.

3 Claims, No Drawings

INSECT- AND MITE-REPELLING METHOD

The invention relates to new morpholinourea derivatives, to a plurality of processes for their preparation, and to their use as insect and mite-repelling agents.

It is the object of agents which repel insects and mites (repellants) to prevent harmful or annoying arthropods from touching, and from stinging and sucking or biting on surfaces which attract them, such as the skin of animals and humans, when this skin has previously been treated with such agents.

A large number of active substances have already been proposed as repellents. (cf., for example, K. H. Büchel in Chemie der Pflanzenschutz- und Schädlingsbekämpfungsmittel [Chemistry of Plant Protection Agents and Pesticides]; editor: R. Wegler, Vol. 1, Springer Verlag Berlin, Heidelberg, N.Y., 1970, p. 487 et seq.).

N,N-Diethyl-3-methyl-benzamide (DEET), dimethyl phthalate and 2-ethyl-hexane-1,3-diol are particularly well known and have been used for some time, of which mainly DEET has gained considerable importance in practice (see, for example, R. K. Kocher, R. S. Dixit, C. I. Somaya; Indian J. Med. Res. 62, 1 (1974)):

Urea derivatives which have an insect-repellent action are furthermore known (see EP-A 22,653; DE-A 2,756,360; U.S. Pat. No. 3,624,204).

A substantial disadvantage of the known repellents is their chronic long-term action, which, in some cases, lasts only for a relatively short time (only a few hours).

New morpholinourea derivatives of the formula (I)

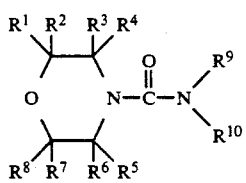

have now been found;
in which the radicals $R^1$ to $R^8$ can be identical or different and represent hydrogen, optionally substituted alkyl, optionally substituted alkenyl, optionally substituted alkynyl, optionally substituted cycloalkyl or optionally substituted phenyl, or where the radicals $R^1$ and $R^4$ and/or $R^5$ and $R^8$ in each case together form a carbocyclic ring,
  $R^9$ represents optionally substituted alkyl, optionally substituted alkenyl, optionally substituted alkynyl, optionally substituted cycloalkyl or optionally substituted benzyl, and
  $R^{10}$ represents hydrogen, optionally substituted alkyl, optionally substituted alkenyl, optionally substituted benzyl or optionally substituted cycloalkyl,
or where $R^9$ and $R^{10}$ together represent an optionally substituted polyalkylene radical which is optionally interrupted by hetero atoms.

Furthermore, it has been found that morpholinourea derivatives of the formula (I)

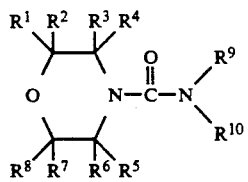

in which the radicals $R^1$ to $R^8$ can be identical or different and represent hydrogen, optionally substituted alkyl, optionally substituted alkenyl, optionally substituted alkynyl, optionally substituted cycloalkyl or optionally substituted phenyl, or where the radicals $R^1$ and $R^4$ and/or $R^5$ and $R^8$ in each case together form a carbocyclic ring,
  $R^9$ represents optionally substituted alkyl, optionally substituted alkenyl, optionally substituted alkynyl, optionally substituted cycloalkyl or optionally substituted benzyl, and
  $R^{10}$ represents hydrogen, optionally substituted alkyl, optionally substituted alkenyl, optionally substituted benzyl or optionally substituted cycloalkyl,
or where $R^9$ and $R^{10}$ together represent an optionally substituted polyalkylene radical which is optionally interrupted by hetero atoms, are obtained by either
  a) reacting morpholines of the formula (II)

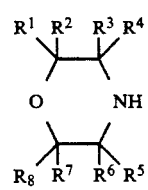

where
  $R^1$ to $R^8$ have the abovementioned meanings, with carbamic acid derivatives of the formula (III)

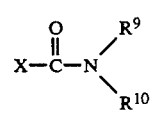

in which
  $R^9$ and $R^{10}$ have the abovementioned meanings and
  X represents a leaving group,
in the presence of a base and in the presence of a solvent, or by
  b) first reacting morpholines of the formula (II)

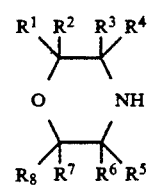

where
  $R^1$ to $R^8$ have the abovementioned meanings, with isocyanates of the formula (IV)

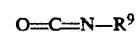

where

R$^9$ has the abovementioned meaning,
in a solvent, and reacting the resulting product of the formula (V)

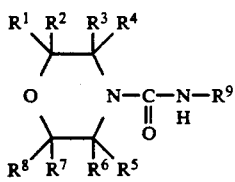

(V)

with an alkylating agent of the formula (VI)

R$^{10}$—X   (VI)

where
R$^{10}$ has the abovementioned meaning
and
X represents a leaving group,
in a solvent and in the presence of a base, or by c) reacting 4-halogenocarbonyl-morpholine derivatives of the formula VII

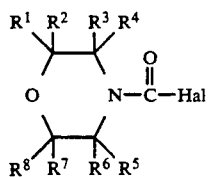

(VII)

where R$^1$ to R$^8$ have the abovementioned meanings, and Hal represents halogen, in particular chlorine, with secondary amines of the formula (VIII)

(VIII)

where
R$^9$ and R$^{10}$ have the abovementioned meanings,
if appropriate in the presence of bases and if appropriate in the presence of solvents.

Furthermore, it has been found that the new morpholinourea derivatives of the formula (I) are distinguished by a highly pronounced insect- and mite-repelling action.

The performance of the repellents is considerably better than that of the repellents known from the prior art. The active substances according to the invention therefore represent a valuable enrichment of the art.

The radicals given in formula (I) preferably have the following meanings:

Optionally substituted alkyl in the radicals R$^1$ to R$^{10}$ is straight-chain or branched and contains preferably 1 to 12 carbon atoms, 1 to 8 being preferred, and, in particular 1 to 6, carbon atoms. Examples which may be mentioned are methyl, ethyl, n- and i-propyl, n-, i- and t-butyl, n-pentyl and n-hexyl.

Optionally substituted alkenyl R$^1$ to R$^9$ represents straight-chain or branched alkenyl having preferably 2 to 10, in particular 2 to 7, carbon atoms. Examples which may be mentioned are optionally substituted ethenyl, propen-1-yl, propen-2-yl, buten-1-yl, buten-2-yl and buten-3-yl.

Optionally substituted alkynyl R$^1$ to R$^9$ represents straight-chain or branched alkynyl having preferably 2 to 6, in particular 2 to 4, carbon atoms. Examples which may be mentioned are optionally substituted ethynyl, propyn-1-yl, propyn-2-yl and butyn-3-yl.

Optionally substituted cycloalkyl R$^1$ to R$^{10}$ represents mono-, bi- and tricyclic cycloalkyl having preferably 3 to 10, in particular 3, 5 or 6, carbon atoms. Examples which may be mentioned are optionally substituted cyclopropyl, cyclobutyl, cyclopentyl, cyclohexyl, cycloheptyl, bicyclo[2.2.1]heptyl, bicyclo[2.2.2]octyl and adamantyl.

Optionally substituted benzyl R$^9$ represents benzyl which is substituted by halogen or alkyl and has preferably 7 to 15 carbon atoms, in particular 7 to 11 carbon atoms. Examples which may be mentioned are: phenylmethyl, 1-methyl-phenylmethyl, and β-methylphenyl)-methyl. Unless otherwise described, halogen always has the meaning of fluorine, chlorine, bromine and iodine, in particular fluorine or chlorine.

The radicals alkyl R$^1$ to R$^{10}$, alkenyl R$^1$ to R$^9$, alkynyl R$^1$ to R$^9$ and cycloalkyl R$^1$ to R$^{10}$ can carry one or more, preferably 1 to 3, in particular 1 or 2, identical or different substituents. Examples of substituents which may be mentioned are: alkoxy having preferably 1 to 4, in particular 1 or 2, carbon atoms such as methoxy, ethoxy, n- and i-propyloxy and n-, i- and t-butyloxy, alkylthio having preferably 1 to 4, in particular 1 or 2, carbon atoms such as methylthio, ethylthio, n- and i-propylthio and n-, i- and t-butylthio; halogenoalkyl having preferably 1 to 4, in particular 1 or 2, carbon atoms, and preferably 1 to 5, in particular 1 to 3, halogen atoms, the halogen atoms being identical or different and the halogen atoms preferably representing fluorine, chlorine or bromine, in particular fluorine, such as trifluoromethyl; hydroxyl, halogen, preferably fluorine, chlorine, bromine and iodine, in particular chlorine and bromine; cyano; nitro, amino; monoalkyl- and dialkyl-amino having preferably 1 to 4, in particular 1 or 2, carbon atoms per alkyl group such as methylamino, methyl-ethyl-amino, n- and i-propylamino and methyl-n-butylamino; carboxyl, carbalkoxy having preferably 2 to 4, in particular 2 or 3, carbon atoms such as carbomethoxy and carboethoxy; sulpho (—SO$_3$H); alkylsulphonyl having preferably 1 to 4, in particular 1 or 2, carbon atoms such as methylsulphonyl and ethylsulphony; and arylsulphonyl having preferably 6 or 10 aryl carbon atoms such as phenylsulphonyl.

Other substituents which the radicals alkyl R$^1$ to R$^{10}$ can carry are cycloalkyl (C$_3$–C$_7$) or phenyl such as, for example, cyclohexylmethyl or benzyl.

The radical phenyl R$^1$ to R$^8$ can carry one or more, preferably 1 to 3, in particular 1 or 2, identical or different substituents. Examples of substituents which may be mentioned are: alkyl having preferably 1 to 4, in particular 1 or 2, carbon atoms such as methyl, ethyl, n- and i-propyl and n-, i- and t-butyl; alkoxy having preferably 1 to 4, in particular 1 or 2, carbon atoms such as methoxy, ethoxy, n- and i-propyloxy and n-, i- and t-butyloxy; alkylthio having preferably 1 to 4, in particular 1 or 2, carbon atoms such as methylthio, ethylthio, n- and i-propylthio and n-, i- and t-butylthio; halogenoalkyl having preferably 1 to 4, in particular 1 or 2, carbon atoms and preferably 1 to 5, in particular 1 to 3, halogen atoms, the halogen atoms being identical or different and the halogen atoms preferably representing fluorine, chlorine or bromine, in particular fluorine, such as trifluoromethyl; hydroxyl; halogen, preferably fluorine, chlorine, bromine and iodine, in particular chlorine and bromine; cyano; nitro; amino; monoalkyl- and dialkylamino having preferably 1 to 4, in particular 1 or 2, carbon atoms per alkyl group such as methylamino, methyl-ethyl-amino, n- and i-propylamino and methyl-n-butylamino; carbonyl; carbalkoxy having preferably 2 to 4, in particular 2 or 3, carbon atoms such as carbomethoxy and carboethoxy; sulpho (—$SO_3H$); alkylsulphonyl having preferably 1 to 4, in particular 1 or 2, carbon atoms such as methylsulphonyl and ethylsulphonyl; and arylsulphonyl having preferably 6 or 10 aryl carbon atoms such as phenylsulphonyl.

In the event that $R^1$ and $R^4$ and/or $R^5$ and $R^8$ in each case together form a carbocyclic ring, $R^1$ and $R^4$ and/or $R^5$ and $R^8$ preferably in each case represent the —($CH_2$)$_3$— and/or the —($CH_2$)$_4$— group.

In the event that $R^9$ and $R^{10}$ together represent a polyalkylene ring which is optionally interrupted by hetero atoms, they together with the included nitrogen atom preferably represent the following 5 to 7-membered, preferably 5 or 6-membered, ring systems: pyrrolidine, piperazine, hexamethyleneimine and morpholine.

Preferred compounds of the formula (Ia)

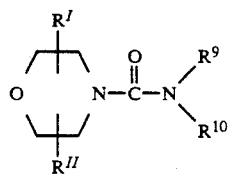

are those in which $R^I$ and $R^{II}$ are identical or different and represent hydrogen, $C_1$-$C_8$-alkyl, $C_2$-$C_8$-alkenyl, $C_3$-$C_6$-cycloalkyl or phenyl, $R^9$ represents optionally $C_1$-$C_4$-alkoxy or halogen-substituted $C_1$-$C_6$-alkyl, $C_2$-$C_6$-alkenyl, $C_3$-$C_6$-alkynyl, $C_3$-$C_8$-cycloalkyl, benzyl or cyclohexylmethyl, and $R^{10}$ represents hydrogen, optionally $C_1$-$C_4$-alkoxy or halogen-substituted $C_1$-$C_6$-alkyl, $C_3$-$C_6$-cycloalkyl or benzyl, or $R^9$ and $R^{10}$ together represent a tetramethylene, pentamethylene, hexamethylene or heptamethylene radical which is optionally interrupted by oxygen and optionally substituted by $C_1$-$C_4$-alkyl.

Particularly preferred are compounds of the formula (Ib)

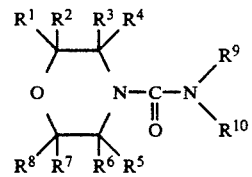

in which $R^I$, $R^{II}$, $R^9$ and $R^{10}$ have the meanings given under formula (Ia).

Furthermore particularly preferred are compounds of the formula (Ia) in which $R^I$ and $R^{II}$ are identical or different and represent hydrogen, methyl or ethyl, and $R^9$ represents $C_1$-$C_6$-alkyl, $C_2$-$C_6$-alkenyl or $C_3$-$C_6$-cycloalkyl, $R^{10}$ represents $C_1$-$C_6$-alkyl or $C_2$-$C_6$-alkenyl.

In addition to the morpholinourea derivatives given in the Preparation Examples, the following may also be mentioned.

General formula (I)

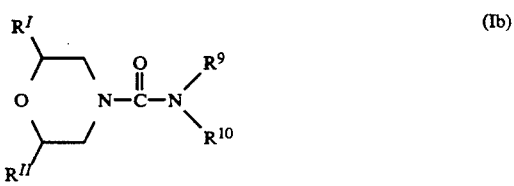

| $R^1$ | $R^2$ | $R^3$ | $R^4$ | $R^5$ | $R^6$ | $R^6$ | $R^7$ | $R^8$ | $R^9$ | $R^{10}$ |
|---|---|---|---|---|---|---|---|---|---|---|
| H | H | H | H | H | H | H | H | H | $CH_3$ | $CH_3$ |
| H | H | H | H | H | H | H | H | H | $CH_3$ | $C_2H_5$ |
| H | H | H | H | H | H | H | H | H | $CH_3$ | n-$C_3H_7$ |
| $CH_3$ | H | H | H | H | H | H | H | H | $CH_3$ | i-$C_3H_7$ |
| $CH_3$ | H | H | H | H | H | H | H | H | $C_2H_5$ | n-$C_4H_9$ |
| $CH_3$ | H | H | H | H | H | H | H | H | $C_2H_5$ | i-$C_4H_9$ |
| H | H | $CH_3$ | H | H | H | H | H | H | $C_2H_5$ | tert.-$C_4H_9$ |
| $CH_3$ | H | H | H | H | H | H | $CH_3$ | H | $C_2H_5$ | sec.-$C_4H_9$ |
| $CH_3$ | H | H | H | H | H | H | $CH_3$ | H | $CH_2$=CH—$CH_2$ | n-$C_4H_9$ |
| $C_2H_5$ | H | H | H | H | H | H | H | H | $CH_2$=CH—$CH_2$ | n-$C_5H_{11}$ |
| $CH_3$ | H | H | H | H | H | H | $CH_3$ | H | n-$C_4H_9$ | i-$C_5H_{11}$ |
| —CH=$CH_2$ | H | H | H | H | H | H | H | H | i-$C_4H_9$ | $C_5H_{11}$ (neo) |
| —CH=$CH_2$ | H | H | H | H | H | H | H | H | sec.-$C_4H_9$ | n-$C_6H_{13}$ |
| 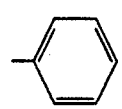 | H | H | H | H | H | H | H | H | n-$C_5H_{11}$ | n-$C_7H_{15}$ |

-continued

General formula (I)

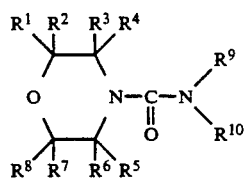

| R¹ | R² | R³ | R⁴ | R⁵ | R⁶ | R⁶ | R⁷ | R⁸ | R⁹ | R¹⁰ |
|---|---|---|---|---|---|---|---|---|---|---|
| Ph | H | H | H | H | H | H | H | H | cyclohexyl | CH₃ |
| H | H | Ph | H | H | H | H | H | H | —CH₂—cyclohexyl | C₂H₅ |
| H | H | CH₃ | H | H | H | H | H | H | —CH₂—Ph | CH₃ |
| Ph | H | Ph | H | H | H | H | H | H | cyclopropyl | n-C₄H₉ |
| Ph | H | Ph | H | H | H | H | H | H | cyclopentyl | C₂H₅ |
| H | H | C₂H₅ | H | H | H | H | H | H | Ph | —CH₃ |
| H | H | C₂H₅ | H | H | H | H | H | H | —CH₂—C≡CH | n-C₄H₉ |
| CH₃ | H | CH₃ | H | H | H | H | H | H | —(CH₂)₅— ||
| C₂H₅ | H | H | H | H | H | H | H | H | —(CH₂)₅— ||
| H | H | C₂H₅ | H | H | H | H | H | H | —(CH₂)₆— ||
| H | H | CH₃ | H | H | H | H | H | H | —(CH₂)₇— ||
| CH₃ | H | H | H | H | H | H | H | H | —(CH₂)₂—O—(CH₂)₂— ||
| CH₃ | H | H | H | H | H | H | H | H | —CH₂CH(CH₃)—O—(CH₂)₂— ||
| H | H | H | H | H | H | H | H | H | —CH₂—Ph | CH₃ |
| H | H | H | H | H | H | H | H | H | —CH₂—Ph | C₂H₅ |
| H | H | H | H | H | H | H | H | H | —CH₂—Ph | C₃H₇-n |
| H | H | H | H | H | H | H | H | H | —CH₂—Ph | C₄H₉-n |

-continued

General formula (I)

$$\begin{array}{c} R^1\ R^2\ R^3\ R^4 \\ \diagdown\diagup\ \diagdown\diagup \\ O\qquad N-C-N \diagup R^9 \\ \diagup\diagdown\ \|\ \diagdown R^{10} \\ R^8\ R^7\ O\ R^6\ R^5 \end{array}$$

| $R^1$ | $R^2$ | $R^3$ | $R^4$ | $R^5$ | $R^6$ | $R^6$ | $R^7$ | $R^8$ | $R^9$ | $R^{10}$ |
|---|---|---|---|---|---|---|---|---|---|---|
| H | H | H | H | H | H | H | H | H | $CH_2\text{—}C_6H_5$ | $CH_2CH=CH_2$ |

In preparation variant a), the morpholines of the formula (II) are reacted with carbamic acid derivatives of the formula (III) in the presence of a base (preferably tertiary organic amine such as, for example, triethylethylamine, nitrogen-containing aromatic substance such as, for example, pyridine, or an inorganic base such as NaOH or KOH, or in the presence of an excess of the morpholine derivative (II)) if appropriate in the presence of a catalyst (such as, for example, 4-dimethylamino-pyridine or 1,3-diazabicyclo(2,2,2)octane (DABCO) and in the presence of a solvent.

Examples of suitable solvents are inert organic solvents such as ethers, benzene and toluene. If appropriate, it is also possible to use water as the solvent or an excess of the morpholine derivative (II) as the solvent.

The reaction temperature is $-20°$ C. to $100°$ C. and preferably $0°$ to $60°$ C.

Each of the reactants (II) and (III) can be employed in excess, but the process is preferably carried out in a molar ratio of (II):(III)=1:1.

In reaction variant b), morpholines of the formula (II) are first reacted with isocyanates of the formula (IV) in a solvent, preferably in an inert organic solvent such as, for example, ether, benzene or toluene, at temperatures of $0°$ to $150°$ C., preferably at $20°$ to $80°$ C. If appropriate, a catalyst is added. An example which may be mentioned is 1,8-diazabicyclo(5,4,0)undec-7-ene (DBU).

The molar ratio morpholine derivative (II):isocyanate (IV) is preferably (1-1.2):1.

The subsequent reaction of the reaction products of the formula (V) with an alkylating agent of the formula $R^{10}$—X (VI) where the leaving group X preferably represents chlorine, bromine or iodine, is preferably carried out in an inert organic solvent.

Examples which may be mentioned are dimethylformamide, dimethyl sulphoxide, ether, acetonitrile or tetrahydrofuran.

Bases which are added are customary inorganic or organic bases. Examples which may be mentioned are: NaOH, KOH, NaH, butyllithium and pyridine.

The reaction temperature is preferably $-20°$ C. to $100°$ C., in particular $20°$ to $80°$ C.

The alkylating agent (VI) can be added in equimolar amount or in up to 5-molar excess to the compound (V).

In reaction variant c), 4-halogenocarbonyl-morpholine derivatives of the formula (VII) are reacted with secondary amines of the formula (VIII). The solvents, bases and catalysts which can be used are the solvents, bases and catalysts described in the above reaction variant a). The reaction conditions correspond to those described in reaction variant a).

The end products of the formula (I) which have been prepared in accordance with process variant a), b) or c) are worked up in a manner known per se, for example by extraction in organic solvents and subsequent distillation or recrystallisation.

The agents according to the invention, which contain at least one derivative of the formula (I), can also contain other insect repellents. Repellents which are suitable are all those which are customary in practice (cf., for example, K. H. Büchel in Chemie der Pflanzenschutz- und Schädlingsbekämpfungsmittel [Chemistry of Plant Protection Agents and Pesticides] editor: R. Wegler, Vol. 1, Springer Verlag Berlin, Heidelberg, N.Y., 1970, p. 487 et seq.).

In the case of repellent combinations, it is preferred to use the morpholinourea derivatives of the general formula (I) together with repellent carboxamides, 1,3-alkanediols and carboxylic esters. The following may be mentioned individually: N,N-diethyl-3-methyl-benzamide (DEET), 2-ethyl-hexane-1,3-diol (Rutgers 612) and dimethyl phthalate.

The insect- and mite-repellent action of the compounds of the general formula (I) is long-lasting.

They can therefore be used with good success for repelling sucking and biting insects and mites which are harmful or a nuisance.

The sucking insects essentially include the mosquitoes (for example Aedes, Culex and Anopheles species), moth gnats (Phlebotomi), buffalo gnats (Culicoides species), blackflies (Simulium species), stinging flies (for example *Stomoxys calcitrans*), tsetse flies (Glossina species), horseflies (Tabanus, Haematopota and Chrysops species), houseflies (for example *Musca domestica* and *Fannia canicularis*), Sarcophagidae (for example *Sarcophaga carnaria*), myiasis-causing flies (for example *Lucilia cuprina, Chrysomyia chloropyga, Hypoderma bovis, Hypoderma lineatum, Dermatobia hominis, Oestrus ovis, Gasterophilus intestinalis, Cochliomyia hominivorax*), bugs (for example *Cimex lectularius, Rhodnius prolixus, Triatoma infestans*), lice (for example *Pediculus humanus, Haematopinus suis, Damalina ovis*), louse flies (for example *Melophagus ovinus*), fleas (for example *Pulex irritans, Ctenocephalides canis, Xenopsylla cheopis*) and sand fleas (for example *Dermatophilus penetrans*).

The biting insects essentially include cockroaches (for example *Blattella germanica, Periplaneta americana, Blatta orientalis, Supella supellectilium*), beetles (for example *Sitophilus granarius, Tenebrio molitor, Dermestes*

*lardarius, Stegobium paniceum, Anobium puntactum, Hylotrupes lucifugus*) and ants (for example *Lasius niger*). The mites include ticks (for example *Ornithodorus moubata, Ixodes ricinus, Boophilus microplus, Amblycmma hebreum*) and mites in the narrow sense (for example *Sarcoptes scabieig, Dermanyssus gallinae*).

The active substances according to the invention, which can be employed undiluted or, preferably, diluted, can be converted into formulations customary for repellents. They can be employed in all administration forms customary in cosmetics, for example in the form of solutions, emulsions, gels, ointments, pastes, creams, powders, sticks, sprays or aerosols from spray cans.

For application in the non-cosmetic sector, the active compounds can be incorporated, for example, into granules, oil sprays or slow-release formulations.

The preparations are prepared in a known manner by mixing or diluting the active compounds according to the invention with solvents (for example xylene, chlorobenzenes, paraffins, methanol, ethanol, isopropanol, water), carriers (for example kaolins, clays, talc, chalk, highly-disperse silica, silicates), emulsifiers (for example polyoxyethylene fatty acid esters, polyoxyethylene fatty alcohol ethers, alkylsulphonates, arylsulphonates) and dispersants (for example lignin, sulphite waste liquors, methylcellulose).

In the formulations, the active compounds according to the invention can be employed as mixtures with each other or, alternatively, in mixtures with other known active compounds (for example sunscreen agents). In general, the preparations contain between 0.1 and 95% by weight of active compound, preferably between 0.5 and 90%.

As a protection against insects or mites which suck blood, the active compounds according to the invention are either applied to the human or animal skin, or clothes and other objects are treated with them.

The active compounds according to the invention are also suitable as an additive to proofing agents for, for example, textile webs, clothes, packaging materials, and as an additive to polishes, cleaners and window cleaners.

The following examples of the preparations and the use of the active compounds according to the invention are intended to further illustrate the invention.

FORMULATION EXAMPLE 1

A repellent in the form of a lotion for dermal application is prepared by mixing 30 arts of one of the active compounds according to the invention, 1.5 parts of perfume and 68.5 parts of isopropanol. Isopropanol can be replaced by ethanol.

FORMULATION EXAMPLE 2

A repellent in the form of an aerosol for spraying onto the skin is prepared by formulating, as a spray can, 50% of active compound solution, consisting of 30 parts of one of the active compounds according to the invention, 1.5 parts of perfume and 68.5 parts of isopropanol, with 50% of Frigen 11/12 (=halogenated hydrocarbon as the propellant).

FORMULATION EXAMPLE 3

Another spray can is composed of 40% of active compound solution consisting of 20 parts of one of the active compounds according to the invention, 1 part of perfume and 79 parts of isopropanol, and 60% of propane/butane (ratio 15:85).

In accordance with Formulation Examples 1, 2 and 3, individual formulations were prepared using the following active compounds: compounds according to Examples 1, 7, 18 and 23.

EXAMPLE A

Repellent test on guinea pig
Test insect: *Aedes aegypti* (imagines)
Number of test insects: about 5,000
Solvent: ethanol (99.8%)

3 parts by weight of active compound are taken in 100 parts by volume of solvent.

A guinea pig whose back has been shaved in an area of 50 $cm^2$ is fixed in a narrow cage (box) in such a way that only the shaved area is accessible to the mosquitoes. After the area has been treated with 0.4 ml of active substance solution, and, after the solvent has evaporated, the guinea pig including box is placed into a cage of dimensions $60 \times 60 \times 60$ cm which contains test insects of both sexes which have only been fed sugar water.

Over a period of 10 minutes, the number of mosquitoes which bite the guinea pig is recorded.

The guinea pig is then removed, and the test is repeated after one hour. The test is carried out over a maximum of 9 hours and until the effect ceases.

A repellent action which is better than the prior art (DEET) is shown here by the compounds of the following examples: Examples 1, 7, 18 and 23.

EXAMPLE B

Repellent test on guinea pigs
Test insect: Culex *pipiens fatigans* (imagines)
Number of test insects: about 1,000
Solvent: ethanol (99.8%)

1 part by weight of active compound is taken in 100 parts by volume of solvent.

A guinea pig whose back has been shaved in an area of 50 cm is fixed in a narrow cage (box) in such a way that only the shaved area is accessible to the mosquitoes. After the area has been treated with 0.4 ml of active substance solution, and, after the solvent has evaporated, the guinea pig including box is placed into a cage of dimensions $60 \times 60 \times 60$ cm which contains test insects of both sexes which have only been fed sugar water.

Over a period of 10 minutes, the number of mosquitoes which bite the guinea pig is recorded.

The guinea pig is then removed, and the test is repeated after one hour. The test is carried out over a maximum of 9 hours and until the effect ceases.

A repellent action which is better than the prior art (DEET) is shown here by the compound of the following example: Example No. 1.

EXAMPLE C

Repellent test on guinea pigs
Test insect: *Stomoxys calcitrans* (imagines)
Number of test insects: about 1,000
Solvent: ethanol (99.8%)

5 parts by weight of active compound is taken in 100 parts by volume of solvent.

A guinea pig whose back has been shaved in an area of 50 $cm^2$ is fixed in a narrow cage (box) in such a way that only the shaved area is accessible to the mosquitoes. After the area has been treated with 0.4 ml of active substance solution, and, after the solvent has evaporated, the guinea pig including box is placed into a cage of dimensions 60×60×60 cm which contains test insects of both sexes which have only been fed sugar water.

Over a period of 10 minutes, the number of mosquitoes which bite the guinea pig is recorded.

The guinea pig is then removed, and the test is repeated after one hour. The test is carried out over a maximum of 9 hours and until the effect ceases.

A repellent action which is better than the prior art (DEET) is shown here by the compound of the following example: Example No. 1.

PREPARATION EXAMPLES

EXAMPLE 1

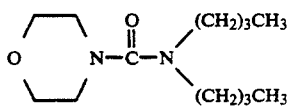

10.4 g (0.12 mol) of morpholine, 0.2 g of 4-dimethylamino-pyridine and 15.2 g (0.15 mol) of triethylamine are dissolved in 250 ml of absolute toluene. 20 g (0.1 mol) of N,N-dibutylcarbamoyl chloride are slowly added dropwise at 0° C. The mixture is stirred for 14 hours at 20° C., and stirring is subsequently continued for 2 hours at 30° C. The triethylammonium chloride which has precipitated is filtered off with suction. The filtrate is washed with dilute hydrochloric acid and water and dried over sodium sulphate, and the solvent is evaporated in vacuo. Bulb-tube distillation gives 21.8 g (86% of theory) of 4-(N,N-dibutylamino-carbonyl)-morpholine as a colorless oil of boiling point 140° C. at 0.2 torr.

EXAMPLE 2

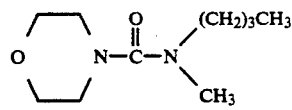

5 g (27 mmol) of 4-(N-butylaminocarbonyl)-morpholine are dissolved in 15 ml of absolute dimethylformamide under a nitrogen atmosphere. 1.7 g (57 mmol) of sodium hydride (80%) are carefully added at 0° C. 5.7 g (40 mmol) of methyl iodide are added, and the mixture is stirred for 2 hours at 40° C.

2 ml of water are added with cooling, and the solvent is evaporated in vacuo. The residue is dissolved in dichloromethane, washed with water and dried over sodium sulphate, and the solvent is then stripped off. Bulb-tube distillation gives 4.6 g (86% of theory) of 4-(N-butyl-N-methylamino-carbonyl)-morpholine in the form of an oil of boiling point 110° C. at 0.15 torr.

EXAMPLE 3

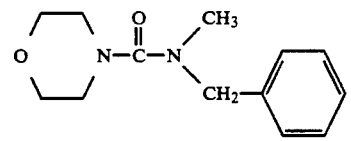

3 g (0.026 mol) of 4-chlorocarbonyl-morpholine are slowly added at 20° C. to 50 ml of N-methylbenzylamine (exothermic reaction). The mixture is stirred for 4 hours at 40° C. and then filtered directly over silica gel (eluent=toluene:acetone=7:3). After the solvent has removed by distillation on a rotary evaporator, 4.4 g (77% of theory) of 4-(N-benzyl-N-methyl-aminocarbonyl)morpholine of refractive index $n_D^{20}=1.5430$ are obtained.

The following compounds were obtained analogously to Examples 1, 2 and 3:

General formula:

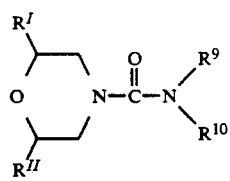

| Example No. | $R^I$ | $R^{II}$ | $R^9$ | $R^{10}$ | Physical data |
|---|---|---|---|---|---|
| 4 | H | H | n-C$_4$H$_9$ | H | m.p.: 72° C. |
| 5 | H | H | n-C$_4$H$_9$ | CH$_3$ | b.p.(0.15 mm): 110° C. |
| 6 | H | H | n-C$_4$H$_9$ | C$_2$H$_5$ | b.p.(0.15 mm): 120° C. |
| 7 | H | H | CH$_2$—CH=CH$_2$ | n-C$_4$H$_9$ | b.p.(0.2 mm): 105° C. |
| 8 | H | H | n-C$_4$H$_9$ | n-C$_4$H$_9$ | b.p.(0.2 mm): 127° C. |
| 9 | H | H | cyclohexyl | CH$_3$ | b.p.(0.13 mm): 150° C. |
| 10 | H | H | —(CH$_2$)$_5$— | | b.p.(0.2 mm): 100° C. |
| 11 | CH$_3$ | H | n-C$_4$H$_9$ | H | b.p.(0.1 mm): 132° C. |
| 12 | CH$_3$ | H | n-C$_4$H$_9$ | CH$_3$ | b.p.(0.2 mm): 129° C. |
| 13 | CH$_3$ | H | n-C$_4$H$_9$ | C$_2$H$_5$ | b.p.(0.2 mm): 100° C. |
| 14 | CH$_3$ | H | CH$_2$—CH=CH$_2$ | n-C$_4$H$_9$ | b.p.(0.5 mm): 128° C. |
| 15 | CH$_3$ | H | n-C$_4$H$_9$ | n-C$_4$H$_9$ | b.p.(0.2 mm): 115° C. |

-continued

General formula:

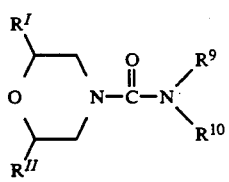

| Example No. | $R^I$ | $R^{II}$ | $R^9$ | $R^{10}$ | Physical data |
|---|---|---|---|---|---|
| 16 | $CH_3$ | H | $C_2H_5$ | $C_2H_5$ | b.p.(0.2 mm): 91° C. |
| 17 | $CH_3$ | H | $n-C_3H_7$ | $n-C_3H_7$ | b.p.(0.2 mm): 110° C. |
| 18 | $CH_3$ | H | —C₆H₁₁ (cyclohexyl) | $CH_3$ | b.p.(0.1 mm): 130° C. |
| 19 | $CH_3$ | H | —$(CH_2)_5$— | | b.p.(0.3 mm): 136° C. |
| 20 | $CH_3$ | $CH_3$ | —$CH_2$—$CH(CH_3)O$—$(CH_2)_2$— | | b.p.(0.1 mm): 119° C. |
| 21 | $CH_3$ | $CH_3$ | —$(CH_2)_5$— | | b.p.(0.3 mm): 112° C. |
| 22 | $CH_3$ | $CH_3$ | $n-C_4H_9$ | H | b.p.(0.3 mm): 155° C. |
| 23 | $CH_3$ | $CH_3$ | $n-C_4H_9$ | $CH_3$ | b.p.(0.2 mm): 130° C. |
| 24 | $CH_3$ | $CH_3$ | $CH_2-CH=CH_2$ | $n-C_4H_9$ | b.p.(0.1 mm): 130° C. |
| 25 | $CH_3$ | $CH_3$ | —C₆H₁₁ (cyclohexyl) | $CH_3$ | b.p.(0.15 mm): 155° C. |
| 26 | H | H | $CH_2$–C₆H₅ | $CH_2$–C₆H₅ | m.p. 107° C. |
| 27 | H | H | $CH(CH_3)C_2H_5$ | $C_4H_9-n$ | $n_D^{20}$: 1.4693 |
| 28 | H | H | $CH(CH_3)C_2H_5$ | $CH(CH_3)C_2H_5$ | |
| 29 | H | H | $CH(CH_3)C_2H_5$ | $CH_2CH=CH_2$ | $n_D^{20}$: 1.4785 |
| 30 | H | H | —C₆H₁₁ (cyclohexyl) | $CH_2CH=CH_2$ | |
| 31 | H | H | $CH_2CH(CH_3)_2$ | $C_4H_9-n$ | $n_D^{20}$: 1.4672 |
| 32 | H | H | $CH_2CH(CH_3)_2$ | $CH_2CH=CH_2$ | $n_D^{20}$: 1.4775 |
| 33 | H | H | $CH_2CH(CH_3)_2$ | $C_4H_9-t$ | |
| 34 | H | H | $CH_2CH(CH_3)_2$ | $CH_2CH(CH_3)_2$ | $n_D^{20}$: 1.4640 |
| 35 | H | H | $CH_2CH(CH_3)C_2H_5$ | $C_4H_9-n$ | $n_D^{20}$: 1.4685 |
| 36 | H | H | $CH_2CH_2OCH_3$ | $CH_2CH_2OCH_3$ | |
| 37 | H | H | $CH_2CH_2OC_2H_5$ | $CH_2CH_2OC_2H_5$ | |
| 38 | H | H | $CH_2CH_2OCH_3$ | $C_4H_9-n$ | |
| 39 | $CH_3$ | H | $CH_2CH_2OC_2H_5$ | $C_3H_7-n$ | |
| 40 | $CH_3$ | $CH_3$ | $CH(CH_3)C_2H_5$ | $CH_3$ | $n_D^{20}$: 1.4687 |
| 41 | $CH_3$ | $CH_3$ | $C(CH_3)_3$ | $CH_3$ | $n_D^{20}$: 1.6480 |
| 42 | $CH_3$ | $CH_3$ | $C_2H_5$ | $CH_3$ | $n_D^{20}$: 1.4689 |
| 43 | H | H | $CH(CH_3)C_2H_5$ | H | m.p.: 124–126° C. |
| 44 | H | H | $n-C_4H_9$ | H | Fp. 74–76° C. |
| 45 | H | H | $CH_2CH(CH_3)_2$ | H | Fp. 94–96° C. |
| 46 | H | H | $C(CH_3)_3$ | H | Fp. 182–184° C. |
| 47 | H | H | $C(CH_3)_3$ | $CH_3$ | Fp. 42–44° C. |
| 48 | H | H | —C₆H₁₁ (cyclohexyl) | H | Fp. 175–177° C. |
| 49 | H | H | $CH(CH_3)C_2H_5$ | $C_2H_5$ | $n_D^{20}$: 1.4692 |
| 50 | H | H | $C(CH_3)_3$ | $C_2H_5$ | $n_D^{20}$: 1.4705 |
| 51 | H | H | $C(CH_3)_3$ | $CH_2CH=CH_2$ | $n_D^{20}$: 1.4740 |
| 52 | H | H | $n-C_4H_9$ | $CH_2CH=CH-CH_3$ | $n_D^{20}$: 1.4885 |
| 53 | H | H | $C(CH_3)_3$ | $n-C_4H_9$ | $n_D^{20}$: 1.4665 |
| 54 | H | H | $n-C_4H_9$ | $CH_2CH=CH_2$ | $n_D^{20}$: 1.4885 |
| 55 | H | H | $CH_2CH(CH_3)_2$ | $CH_2CH=CH-CH_3$ | $n_D^{20}$: 1.4805 |
| 56 | $CH_3$ | H | $CH_2CH(CH_3)_2$ | H | $n_D^{20}$: 1.4781 |

-continued

General formula:

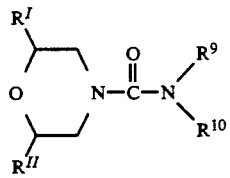

| Example No. | $R^I$ | $R^{II}$ | $R^9$ | $R^{10}$ | Physical data |
|---|---|---|---|---|---|
| 57 | $CH_3$ | H | $CH_2CH(CH_3)_2$ | $n-C_4H_9$ | $n_D^{20}$: 1.4672 |

It will be understood that the specification and examples are illustrative but not limitative of the present invention and that other embodiments within the spirit and scope of the invention will suggest themselves to those skilled in the art.

We claim:

1. A method of repelling insects and mites which comprises applying to a surface from which it is desired to repel such insects and mites an insect- and mite-repelling effective amount of a compound of the formula (Ia)

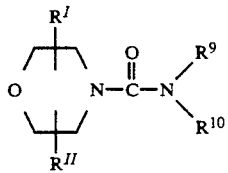

in which $R^I$ and $R^{II}$ are identical or different and represent hydrogen, $C_1-C_6$-alkyl, $C_2-C_6$-alkenyl, $C_3-C_6$-cycloalkyl or phenyl, $R^9$ represents optionally $C_1-C_4$-alkoxy or halogen-substituted $C_1-C_6$-alkyl, $C_2-C_6$-alkenyl, $C_3-C_6$-alkinyl, $C_3-C_6$-cycloalkyl, benzyl or cyclohexylmethyl, and $R^{10}$ represents hydrogen, optionally $C_1-C_4$-alkoxy or halogen-substituted $C_1-C_6$-alkyl, $C_3-C_6$-cycloalkyl or benzyl, or $R^9$ and $R^{10}$ together represent a tetramethylene, pentamethylene, hexamethylene or heptamethylene radical which is optionally interrupted by oxygen and optionally substituted by $C_1-C_4$-alkyl.

2. A method according to claim 1 wherein
$R^I$ and $R^{II}$ are identical or different and represent hydrogen, methyl or ethyl, $R^9$ represents $C_1-C_6$-alkyl, $C_2-C_6$-alkenyl or $C_3-C_6$-cycloalkyl, and $R^{10}$ represents $C_1-C_6$-alkyl or $C_2-C_6$-alkenyl.

3. A method according to claim 1 wherein the compound is
4-(N,N-dibutylamino-carbonyl)-morpholine,
4-(N-allyl-N-n-butyl-aminocarbonyl)-morpholine,
2-methyl-4-(N-cyclohexyl-N-methyl-amino-carbonyl)-morpholine or
2,6-dimethyl-4-(N-n-butyl-N-methyl-amino-carbonyl)-morpholine.

* * * * *

UNITED STATES PATENT AND TRADEMARK OFFICE
CERTIFICATE OF CORRECTION

PATENT NO. : 5,218,002
DATED : June 8, 1993
INVENTOR(S) : Stroech, et al.

It is certified that error appears in the above-identified patent and that said Letters Patent is hereby corrected as shown below:

Col. 18, line 20  After " $C_1-C_6$-alkyl, " insert -- $C_2-C_6$-alkenyl --

Signed and Sealed this

Twenty-sixth Day of April, 1994

Attest:

BRUCE LEHMAN

Attesting Officer        Commissioner of Patents and Trademarks